United States Patent [19]

Juhos et al.

[11] Patent Number: 5,037,641

[45] Date of Patent: Aug. 6, 1991

[54] BEAUTY PREPARATIONS HAVING ANTI-FADING EFFECT AND A PROCESS FOR PREPARING THE SAME

[75] Inventors: Tibor Juhos; Veronika Pál; Éva Wladimir née Pap; Ilona Kristóf née Szvitil; Zsuzsanna Emri née Hársy; Gabriella Papp née Iski; Csaba Varga, all of Debrecen, Hungary

[73] Assignee: Biogàl Gyogyszergyàr, Debrecen, Hungary

[21] Appl. No.: 172,566

[22] Filed: Mar. 24, 1988

[51] Int. Cl.$^5$ .................. A61K 7/42; A61K 7/44; A61K 35/78
[52] U.S. Cl. ...................................... 424/59; 424/60; 424/195.1; 514/844
[58] Field of Search ................ 424/60, 62, 195.1, 59; 514/844

[56] References Cited

U.S. PATENT DOCUMENTS 4,460,488  7/1984  Grollier et al. ............... 424/47 X
4,559,225 12/1985  Fourman ........................ 424/60 X
4,737,360  4/1988  Allen et al. ................... 424/60

OTHER PUBLICATIONS

Back, *The Illustrated Herbal*, pp. 56-57 (1987).

Primary Examiner—John W. Rollins
Attorney, Agent, or Firm—Schweitzer, Cornman & Gross

[57] ABSTRACT

The invention relates to cosmetics having UV-screening (sunscreen) effect, a process for preparing, and process of protecting skin. The cosmetic comprises elder blossom extract as the active ingredient together with cosmetically acceptable diluent and/or carriers, and optionally, with p-dimethylaminobenzoic acid 2-ethylhexylester.

11 Claims, No Drawings

BEAUTY PREPARATIONS HAVING ANTI-FADING EFFECT AND A PROCESS FOR PREPARING THE SAME

FIELD OF THE INVENTION

The present invention relates to UV-screening (sunscreen) cosmetics, a process for preparing the same, and a process for protecting skin therewith. The cosmetics of the invention comprise the extract of elder blossom as active ingredient together with nontoxic diluents and/or carriers and optionally p-dimethylaminobenzoic acid 2-ethyl-hexylester.

BACKGROUND OF THE INVENTION

The wide variety of commercially available cosmetic products comprising synthetic or natural substances as active ingredient is primarily offered for assuring the smoothness, fineness, and recovery of the original natural condition of skin. However, the number and assortment of beauty products is restricted which have not only favorable effect on skin but also exhibit UV-screening activity.

Light can cause a wide variety of transformations of skin. The symptoms can range from the appearance of cosmetically unpleasant pigment marks such as age spots and freckles on the healthy but sun-sensitive skin through the slight or more serious inflammation of skin to even as severe as photodermatosis. The underlying disease is usually not cured, but only symptomatic treatment is carried out, such as by protecting the skin from sunlight.

Both the appearance of pigment marks and the underlying pathological processes are caused by rays in the UV-B (290–310 nm) and UV A (315–400 nm) wavelength ranges. In this interval the range of 280–320 nm is considered the most dangerous. (New Scien., 31.228/1969). Therefore, it is desirable that the light absorbing capacity of good UV-screening substances should extend over a wide wavelength range.

Numerous compounds proved to have UV-screening activity. Most of them can absorb light rays falling into the UV-B wavelength range (Derm. Wochen 52,313). There are much fewer compounds which are also effective in the UV A wavelength range.

The compounds absorbing the UV-B range, which absorb the pigment-forming rays are primarily cosmetic light filters, while those compounds which absorb rays of the UV B range generally exhibit therapeutic activity as well.

In our experiments we searched for a natural active ingredient of vegetable origin which is inexpensive, is easy to obtain, has a favorable effect on skin, and has a suitable light absorbing ability. The extract of elder blossom proved to be the most suitable for this purpose.

Black elder blossom (Sambucus nigra) belonging to the family of elder-flowers (Caprifoliaceae) is a known medical herb. Its fruits or flowers have been used for a long time to prepare herbal teas. (Rápóti, Romvári: Gyógyitó Növények [medical plants], Medicina [Publisher] Budapest, Hungary, 1969). It smells sweetly and can be used to flavor consumer goods, soft drinks, wines, etc. (German Patent No. 2,031,145).

The small, yellowish white, typically pleasant smelling flowers of elder blossom are extremely rich in biologically active compounds, volatile oils, flavorants (Planta Medica 31, 365–370, 1983).

In addition to the volatile oils, such as linalol, geraniol, eugenol, perargonic acid esters, etc. that cause the pleasant smell, the flower of elder blossom also comprises numerous biologically important compounds which favorable effect on skin, enabling its use in cosmetics. From such substances e.g.:

- kolin and rutin are compounds of a vitamin type;
- cholesterol, stigmasterol, sitosterol are the natural ingredients of skin which are also used in cosmetic industry as natural emulsifiers;
- the polysaccharides have antiphlogistic agent;
- methyl salicylate is also an antiphlogistic agent;
- emulsin is an enzyme; and
- sambunigrin is a glycoside which plays an important role min the regeneration of epithelic cells.

The elder blossom flower also comprises compounds of antiseptic activity (carvakrol, thymol). Thymol is by about an order of magnitude more effective than phenol against the pyogenic bacteria. In addition, it also possesses an anti-rancidity and germicidal effect.

Further ingredients of elder blossom flower that are worth mentioning from a cosmetic point of view are tannin, catechol, and other tanning materials having an emphractic feature, also fatty acid esters, and waxes forming a natural protective layer on the surface of the skin.

Our aim was to produce beauty products for the treatment of the face and body which are not only of a cosmetic nature, but also have a UV-screening effect.

SUMMARY OF THE INVENTION

We found that cosmetics containing extract of elder blossom flower as active ingredient in admixture with cosmetically acceptable carriers and/or diluents in about 3–5 times the weight based on the elder blossom extract, and optionally about 2–10% by weight of p-dimethylaminobenzoic acid 2-ethyl-hexylester proved to meet these foregoing requirements.

The cosmetics according to the invention are prepared by extracting elder blossom flowers with water or a mixture of water and alcohol, and homogenizing the extract with one or more nontoxic, cosmetically acceptable carrier and/or diluent, and optionally with from about 2% to about 10% by weight of p-dimethylaminobenzoic acid 2-ethyl-hexyl-ester.

DETAILED DESCRIPTION OF THE INVENTION

The elder-blossom flower extract absorbs light within the wavelength range of 200–360 nm. This range is broad enough that a composition comprising the said extract can be used to prevent the effect not only of UV-B rays, but also partly of UV A rays.

The UV-screening activity of elder blossom flower extract can primarily be attributed to the light absorbing activity of cumarin derivatives, methyl salicylate, and quercetin (3,3',4,5,7-pentahydroxyflavone) all in elder blossom.

One of the light absorbing compound groups of vegetable origin are the 7-alkoxy cumarines with an absorption maximum of around 370 nm. The UV-screening activity of methyl salicylate has also been known (U.S. Pat. No. 2,435,055). Quercetin exhibits not only light absorbing activity, but it is also preferred as an antioxidant in view of the stability of the composition.

According to our invention the elder blossom extract is prepared by extracting the collected and optionally dried elder blossom flowers with water or a mixture of water and alcohol. The extraction is carried out under mild condition between about 15° and 50° C., such as by soaking the flowers at 40°-50° C. for 24 hours, or by stirring the flowers in the extrahand for 6-8 hours.

For the preparation of the extract 3-10 times the weight of water, or mixture of water and alcohol is used based on the amount of dried elder blossom flower. A mixture comprising 10-20% by volume, at most 40% by volume alcohol with the rest being water is a suitable composition for the extrahand.

The efficiency of the extraction can be enhanced by pre-soaking the flowers in aqueous solution of 5-10% by weight of sugar, preferably sorbitol, or in a mixture of water and alcohol.

The solid vegetable residue is removed form the extract by filtration, and the extract comprising the active ingredient can be immediately used, or it can be stored suitably at a temperature of about 5°-10° C. The extract can be stored at such a relatively cool temperature for a practically unlimited time.

The cosmetic according to the invention is prepared by mixing the extract comprising the active ingredient, with about 4-5 times its weight with a diluent and/or carrier calculated for the amount of the extract. The diluents and carriers are chosen depending on the alcohol content of the extract and its intended use (face-cream, body lotion, hydrating ampoule, etc.)

The UV-screening activity of the cosmetics comprising elder blossom extract can favorably influenced by the addition of p-dimethylaminobenzoic acid 2-ethyl-hexylester, therefore the UV-screening composition can optionally include from about 2% to about 10% by weight of p-dimethylaminobenzoic acid 2-ethyl-hexylester. The optimum amount of this compound depends on the type of skin (normal, sensitive, etc.) and the type of cosmetic to be prepared (face cream, body lotion, suntan lotion, etc.).

The invention is further disclosed by way of the following illustrative examples.

EXAMPLE 1

300 g of dried elder blossom flower are soaked in 1 liter of deionized aqueous solution of 50 g sorbitol, at a temperature of 20°-25° C. for 48 hours. The vegetable particles are removed by filtration and the rest of the solution is used as active ingredient.

EXAMPLE 2

300 g of dried elder blossom flower are stirred in a 3 liter solution of deionized water comprising 150 g of sorbitol, at a temperature of 40°-45° C. for 6 hours. The solution is cooled to 20°-25° C., filtered and used as active ingredient.

EXAMPLE 3

300 g of dried elder blossom flower are stirred in 1 liter of deionized water comprising 100 g of fructose at 40°-45° C. for 24 hours. The solution is cooled to 20°-25°, filtered and used as active ingredient.

EXAMPLE 4

300 g of dried elder blossom flower are stirred for 8 hours in a mixture of 1350 ml of water and 150 ml of ethanol having dissolved in it 75 g sorbitol, at a temperature of 15°-20° C. The solution is filtered off and used as active ingredient.

EXAMPLE 5

300 g of dried elder blossom flower are soaked for 48 hours in a mixture of 650 ml of water and 350 ml of ethanol having dissolved in it 80 g of sorbitol at a temperature of 15° to 20° C. The solution is filtered off and used as active ingredient.

EXAMPLE 6

Preparation of Face Cream I

| Composition: | |
|---|---|
| active ingredient | 61 g |
| hydromyristenol | 10 g |
| Emulsan MD* | 10 g |
| cetearyl octanoate | 3 g |
| sorbitan sesquioleate | 5 g |
| caprylic/capric triglyceride | 5 g |

*a surfactant/emulsifier which is a partial glyceride of a fatty acid, sold by Henkel KGaA.

The above ingredients except the active ingredient are charged into a rustproof vessel and maintained on a water-bath at a temperature of 65°-70° C. under steady slow stirring until it becomes homogenous. Then the mass is gradually cooled to 45°-50° C. and the active ingredient of any one of Examples 1 to 3 is added. The mixture is cooled to a temperature of 25° C. under further stirring, it is mixed with a solution of 0.95 g ethanol, 0.015 g of propylparaoxybenzoate and 0.035 g of methylparaoxybenzoate, 5 g of polyoxyethylene-(100)-stearate, and perfume.

EXAMPLE 7

Preparation of Face Cream II

| Composition: | |
|---|---|
| active ingredient | 59 g |
| hydromyristenol | 10 g |
| Emulsan MD | 10 g |
| sorbitan sesquioleate | 5 g |
| cetearyl octanoate | 3 g |
| caprylic/capric triglyceride | 5 g |

The above ingredients are mixed according to Example 6 except that the appropriate quantity of the active ingredient prepared according to Example 4 or 5 is added, followed by 2 g of p-dmethylaminobenzoic acid 2-ethyl-hexylester and the mixture is homogenized.

EXAMPLE 8

Body Lotion

| Composition: | |
|---|---|
| active ingredient | 95 g |
| PEG-7 hydrogenated castor oil | 6 g |
| microcrystalline wax | 2 g |
| hydrogenated polyisobutene | 15 g |
| caprylic/capric triglyceride | 5 g |

The above ingredients, except the active ingredient, are charged into a rustproof vessel and mixed on a water-bath at a temperature of 65°-70° C. under stirring. Then the melt is gradually cooled to a temperature of 45°-50° C. and the desired amount of the active ingredient prepared according to Example 4 or 5, is added, together with 5 g of p-dimethylaminobenzoic acid 2- ethyl-hexylester. The mixture is further cooled to 25° C. and 3 g of propyleneglycol, 0.5 g of magnesium sulfate (MgSO$_4$.7H$_2$O)$_1$ and perfume are added and the mixture is homogenized.

EXAMPLE 9

Sunning Lotion

| Composition: | |
|---|---|
| active ingredient | 90 g |
| Protegin* | 24 g |
| caprylic/capric triglyceride | 5 g |

*water-bonding nonionic emulsifier cream base, sold by Goldschmidt Co.

The above ingredients are mixed at a temperature of 40°–45° C. under stirring. As active ingredient any of the active ingredients prepared according to Examples 1 to 5 can be used. Then 10 g of p-dimethylaminobenzoic acid 2-ethyl-hexylester are added to the mixture, which is then cooled to 20°–25° C., and homogenized with perfume.

It was found that the permanent use of cosmetics in accordance with the present invention favorably influences the epithelization of skin, regenerates the lipid shell of skin, enhanced the elasticity of horn layer, reduces the stagnation of the blood-vessel system of true skin and stops the slighter inflammatory processes in skin. The polysaccharides that dissolve in water while swelling have an effect on the water household of skin, they increase in volume of the horn cells, thus enhance the water absorbing capacity of cells and promote the smoothing of facial lines and wrinkles.

The light-absorbing materials obtained from elder blossom flowers by the process of the invention, according to our experience, absorb light between the wavelengths of 200 and 360 nm, they protect the skin from UV rays that cause erythema, and partly filter the directly tanning rays as well. Permanent use of the cosmetics of the invention, especially during the more intensively sunny months, prevents the appearance of freckles and age spots.

We claim:

1. A method for protecting skin against the effect of UV radiation, which comprises applying to the skin a composition comprising elder blossom extract as the active ingredient.

2. The method of claim 1, wherein said composition further comprises from about 2% to about 10% by weight, based on the composition, of p-dimethylaminobenzoic acid 2-ethylhexylester.

3. The method of claim 2, wherein said composition further comprises from about 3 times to about 5 times the weight of said elder blossom extract in said composition, of at least one of a cosmetically acceptable carrier, a cosmetically acceptable diluent, or both such carrier and such diluent.

4. Sunscreen composition which comprises elder-blossom extract as the active ingredient, further comprising from about 3 to about 5 times the weight of said active ingredient of at least one of a cosmetically acceptable carrier, a cosmetically acceptable diluent, or both such carrier and such diluent, and from about 2% to about 10% by weight based on said composition, of p-dimethylaminobenzoic acid 2-ethylhexylester.

5. Process for preparing a sunscreen composition, which comprises extracting elder-blossom (Sambucus nigra) with water or with an aqueous solution of a cosmetically acceptable alcohol, and mixing the extract with at least one of a cosmetically acceptable diluent, a cosmetically acceptable carrier, or both such a diluent and such a carrier.

6. The process of claim 5, wherein said extracting is carried out at a temperature from about 15° C. to about 45° C.

7. The process of claim 5, wherein from about 3 to about 10 times based on the weight of dried elder blossom of water, or of an aqueous solution of an alcohol, is used as the extracting agent.

8. The process of claim 5, wherein the extracting agent in said extraction comprises from about 10% to about 40% by volume of said cosmetically acceptable alcohol.

9. The process of claim 5, wherein the extracting agent in said extraction comprises an aqueous solution of from about 5% to about 10% by volume of a sugar.

10. The process of claim 5, wherein the extracting agent in said extraction comprises an aqueous solution of from about 5% to about 10% by volume of sorbitol.

11. The process of claim 5, wherein said diluent, carrier, or both diluent and carrier comprise from about 3 times to about 5 times the amount of the amount of said extract, and further comprising adding from about 2% to about 10% wt. based on the composition of p-dimethylaminobenzoic acid 2-ethylhexylester.

* * * * *